United States Patent
Edwards et al.

(10) Patent No.: US 6,530,904 B1
(45) Date of Patent: Mar. 11, 2003

(54) MEDICAL INJECTOR

(76) Inventors: Evan T. Edwards, 221 Bollingbrook Ct., Richmond, VA (US) 23236; Eric S. Edwards, 221 Bollingbrook Ct., Richmond, VA (US) 23236

( * ) Notice: Subject to any disclaimer, the term of this patent is extended or adjusted under 35 U.S.C. 154(b) by 0 days.

(21) Appl. No.: 09/907,609

(22) Filed: Jul. 19, 2001

Related U.S. Application Data

(60) Provisional application No. 60/225,413, filed on Aug. 15, 2000.

(51) Int. Cl.$^7$ ................................................ A61M 5/32
(52) U.S. Cl. ...................................... 604/197; 604/195
(58) Field of Search ................................ 604/185, 192, 604/194, 195, 196, 197, 198, 218, 212, 110, 181, 187, 272

(56) References Cited

U.S. PATENT DOCUMENTS

| | | |
|---|---|---|
| 4,360,019 A | 11/1982 | Portner et al. |
| 4,484,910 A | 11/1984 | Sarnoff et al. |
| 4,624,660 A | 11/1986 | Mijers et al. |
| 4,673,657 A | 6/1987 | Christian |
| 5,085,642 A | 2/1992 | Sarnoff |
| 5,286,258 A | 2/1994 | Haber et al. |
| 5,343,519 A | 8/1994 | Feldman |
| 5,645,534 A | 7/1997 | Chanoch |
| 5,769,213 A | 6/1998 | Chatterton |
| 5,832,488 A | 11/1998 | Eberhardt |
| 5,837,546 A | 11/1998 | Allen et al. |
| 5,875,413 A | 2/1999 | Vinci |
| D407,487 S | 3/1999 | Greubel et al. |
| 5,925,021 A | 7/1999 | Castellano et al. |
| 6,102,896 A * | 8/2000 | Roser ........................ 604/218 |

* cited by examiner

*Primary Examiner*—Manuel Mendez
(74) *Attorney, Agent, or Firm*—Michael N. Haynes

(57) ABSTRACT

A medical injector apparatus is provided for carrying medications, for example epinephrine. The medical injector includes a safety guard, and a housing having a first casing portion and a second casing portion which are secured together to form a chamber therebetween. A pair of hinge portions provides pivoting motion of a safety guard. The pusher bar is not attached to the housing and is free to move within the chamber provided. A leaf spring is disposed between the stationary bar and the pusher bar to resiliently bias the pusher bar so as to be in a non-dispensing condition. The pusher bar is connected to a column which passes through an aperture in a stationary bar. The column is connected directly to a wedge-shaped member. A needle is secured to the wedge shaped member. The wedge-shaped member is shaped to conform to a wedge-shaped reservoir formed in a portion of the housing chamber, and the medication fluid is disposed in the reservoir located between the wedge-shaped member and the inclined sides housing chamber. The reservoir is sized to contain a precisely defined volume of medication fluid. The bottom portion of the housing also includes a resilient sleeve disposed in a bore formed in the bottom portion of the housing, for protecting a needle. The needle is secured into the wedge-shaped member. The needle passes through the resilient sleeve when the pusher bar is depressed.

24 Claims, 3 Drawing Sheets

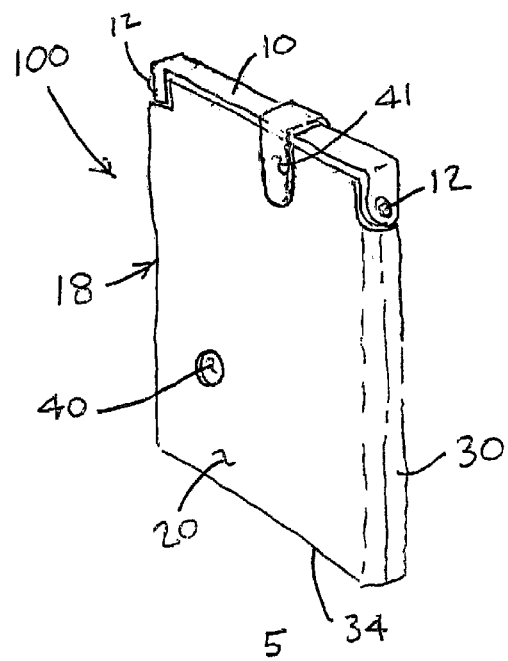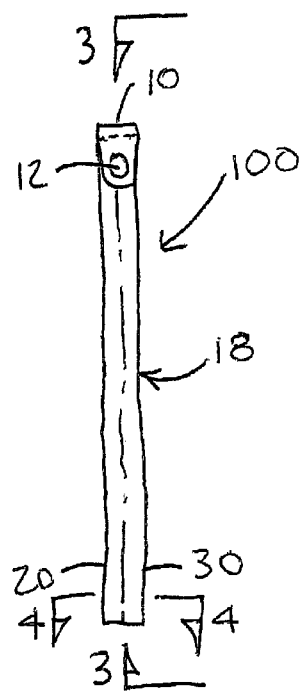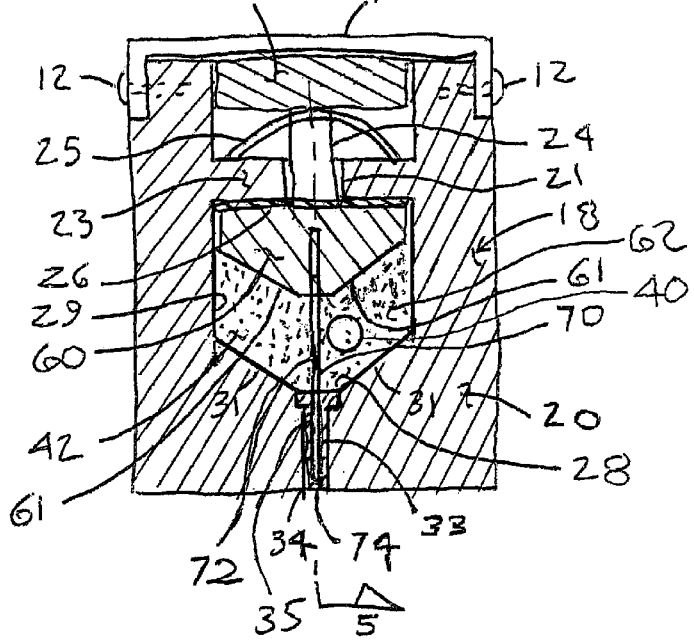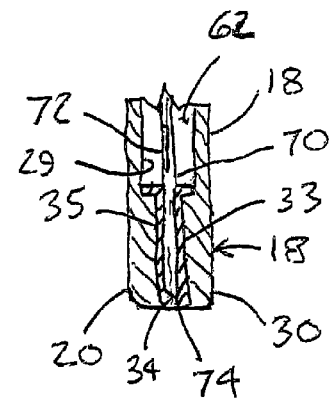

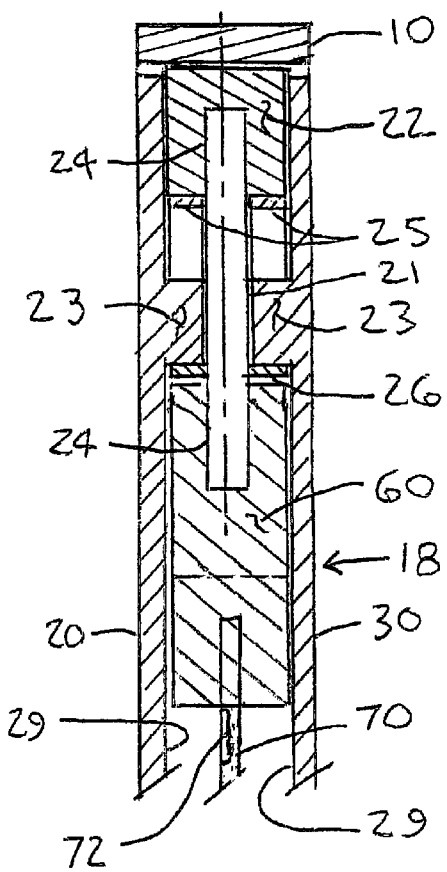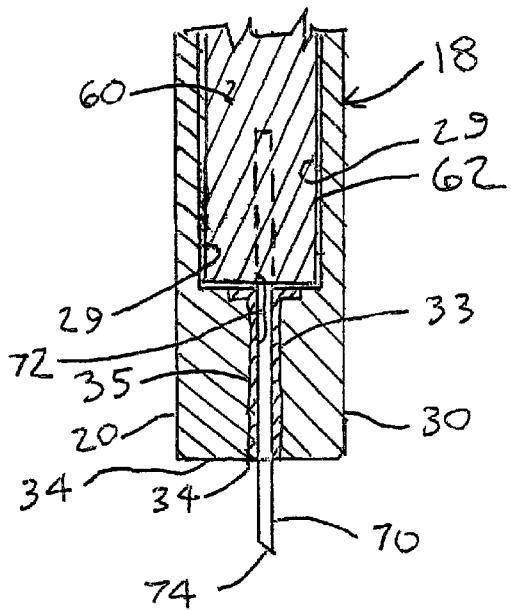
FIG. 5
FIG. 6

MEDICAL INJECTOR

This Utility Patent Application claims priority of Provisional Patent Application, 60/225,413 filed Aug. 15, 2000, and this Provisional Patent Application is incorporated by reference herein.

FIELD OF THE INVENTION

The present invention relates to medical injectors suitable for use with medication which must be injected. More particularly, the invention relates to a disposable credit card sized injector, suitable for carrying in a wallet or pocket.

BACKGROUND OF THE INVENTION

The use of medical injectors such as syringes is well known in the medical arts. However, there is a problem in that such injectors cannot readily be carried on the person of a user, due to the risk of breakage and the lack of appropriate safeguards to protect a casual or unsophisticated user.

For example, glass vial syringes are susceptible of breakage. Further, cylindrical medical injector like syringes are too bulky to carry in a pocket, let alone to carry inside a wallet.

U.S. Pat. No. 5,286,258 issuing to Terry Haber on Feb. 15, 1994 discloses a multipharmaceutical delivery system for simultaneous delivery of two or more pharmaceuticals through a pivoting needle. The overall shape is similar to a credit card.

U.S. Pat. No. 5,837,546 issuing to Michael Allen on Nov. 17, 1998 discloses an electronic assay device for determining the presence of one or more selected analytes in a sample.

U.S. Pat. No. 5, 832,488 issuing to Silvio Eberhardt on Nov. 3, 1998 discloses a computer system and method for storing medical histories using a smartcard to store data.

U.S. Pat. No. 4,484,910 issuing to Stanley Sarnoff et al on Nov. 27, 1984 discloses a dual mode automatic injector with a safety position.

Accordingly, there is a need in the art for a convenient medical injector which is easy to carry and safe to use, is inexpensive, disposable and can be carried in a pocket or even in a wallet of a user.

SUMMARY OF THE INVENTION

From the foregoing, it is seen that it is a problem in the art to provide a device meeting the above requirements. According to the present invention, a device is provided which meets the aforementioned requirements and needs in the prior art. Specifically, the device according to the present invention provides a convenient medical injector which is easy to carry and safe to use, and which can be carried in a pocket or even in a wallet of a user.

More particularly, the medical injector according to the present invention is useful for carrying pharmaceuticals including, but not limited to, epinephrine, insulin medication, anti-nerve gas agent, snake bite anti-venom, heart medications, allergy medication, and various emergency medications such as atropine and lidocaine.

The medical injector includes a safety guard, a housing formed of a first casing portion secured to a second casing portion. A pair of hinge portions provides pivoting motion of a safety guard. A window may be provided to observe the medication fluid stored within the wedge shaped reservoir. The safety guard protects a pusher bar from accidental actuation.

The pusher bar is not attached to the housing, and is free to move relatively thereto. The pusher bar is connected to a column which passes through an aperture in the stationary bar. The column is connected directly to a wedge-shaped member which carries a needle.

A spring means is disposed between the stationary bar and the pusher bar to resiliently bias the pusher bar into a non-dispensing condition. The wedge-shaped member is shaped to conform to a wedge-shaped recess formed in the lower casing portion, and the medication fluid is disposed in the space between, the wedge-shaped member and the lower inclined portion of the housing. This space is thus a precisely defined volume, containing a precise amount of the medication fluid.

A resilient sleeve is disposed in a bore formed in the bottom portion of the housing for protecting a needle. The needle is fixed into the wedge-shaped member. The needle passes through the rubber or plastic sleeve when the pusher bar is depressed to cause movement of the wedge-shaped member. When the pusher bar is depressed, the needle penetrates through the resilient sleeve, and extends beyond the bottom portion of the housing.

Other objects and advantages of the present invention will be more readily apparent from the following detailed description when read in conjunction with the accompanying drawings.

BRIEF DESCRIPTION OF THE DRAWINGS

FIG. 1 is a perspective view of a medical injector according to the present invention.

FIG. 2 is a side elevational view of the medical injector of FIG. 1.

FIG. 3 is a sectional view taken along line 3—3 of FIG. 2.

FIG. 4 is a sectional view taken along line 4—4 of FIG. 3.

FIG. 5 is an enlarged sectional view of actuator elements and leaf springs, taken along line 5—5 of FIG. 3.

FIG. 6 is a side elevational view of the bottom portion of the medical injector of FIG. 1 wherein a needle portion projects from the bottom wall of a lower casing portion.

DETAILED DESCRIPTION OF THE INVENTION

Figure 7:
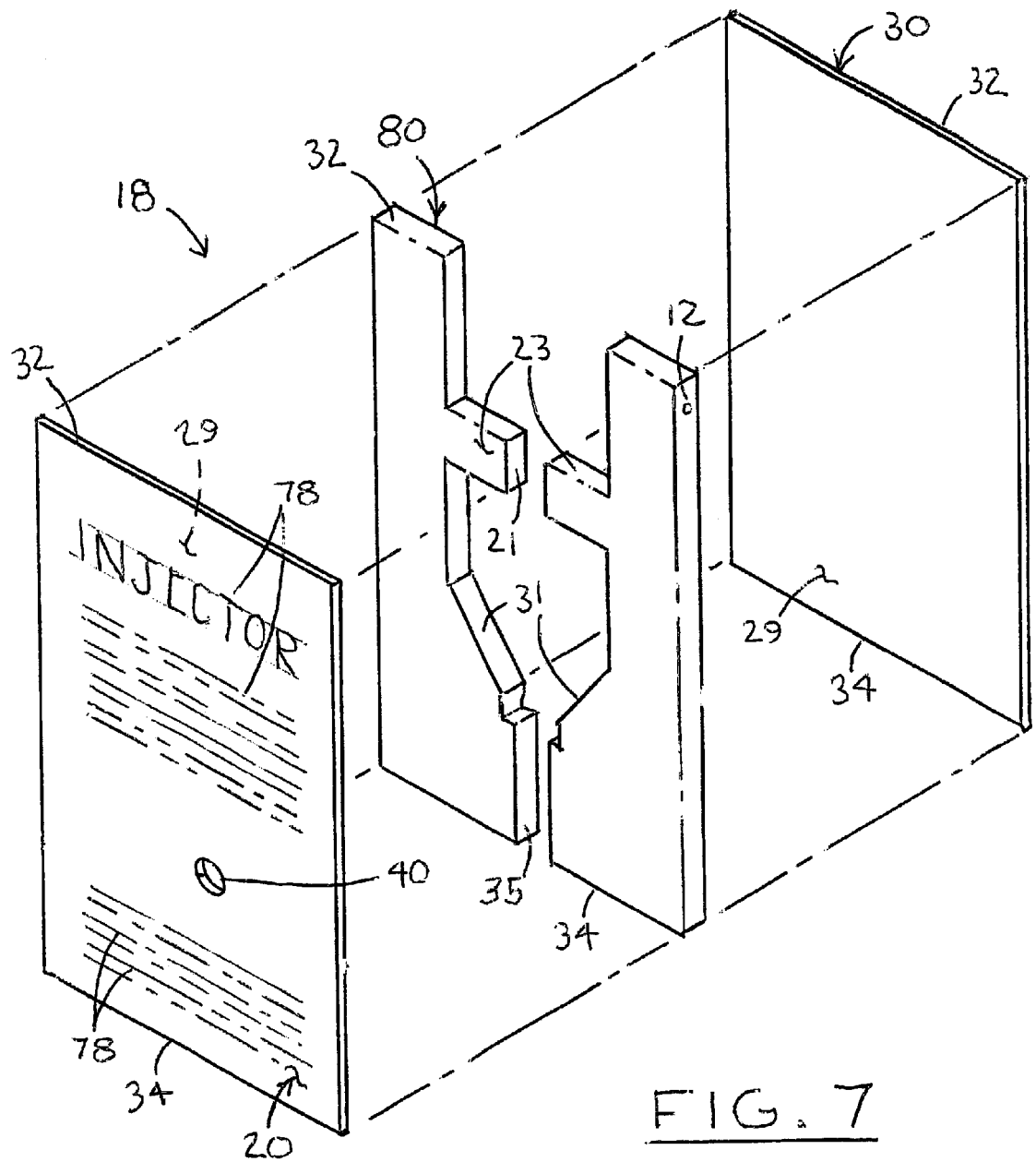
FIG. 7 is an exploded view of the medical injector apparatus, showing a first casing side, a central housing member and a second casing side, which are secured together to form the medical injector apparatus housing.

A medical injector apparatus 100 is shown in FIG. 1. The medical injector apparatus 100 includes a housing 18 having a first casing portion 20, and a second casing portion 30. The first casing portion 20 and the second casing portion 30 are sealed together by any known leak-proof means, such as with adhesive, by heat sealing, by laser bonding, by ultrasonic welding, by fusing, etc. A chamber 28 is formed between the first casing portion 20 and the second casing portion 30, as shown in FIG. 3.

A wedge shaped member 60 having inclined sides 61, 61 is slidably received within the chamber 28. The wedge shaped member 60 may be made of a resilient material, such as rubber, to provide a sliding seal between the interior walls 29 of first casing portion 20 and the second casing portion 30. Alternatively, a flexible seal 26 may be secured to the wedge shaped member 60 to provide a sliding liquid tight seal between the wedge shaped member 60 and the interior walls 29 of the chamber 28. A fluid tight seal may also be formed between the column 24 and the stationary bar 23.

A safety guard 10 is pivotally mounted to the housing with a pair of hinge portions 12, 12. The hinge portions 12, 12 provide a pivoting motion of the safety guard 10 about an axis which connects the hinge portions 12, 12.

The first casing portion 20 preferably has a window 40 therein, which is made of a material which permits inspection of medication fluid 42 inside the medical injector 100, but which does not permit passage of harmful rays therethrough. For example, the material of the window 40 should block UV rays. The window 40 can be composed of a glass or plastic material, for example, coated on one side (the side not in contact with the medication fluid 42) to have a UV-blocking coating. For certain medication fluids, it is necessary to block much of the ambient light as well, and therefore the window 40 may be darkened somewhat, similarly to smoked glass.

Alternately, a breakable seal 41 may be used to secure the safety guard 10 to the housing 18, in place over the pusher bar 22 in its raised position. The breakable seal 41 is broken when the safety guard 10 is biased about hinge portions 12,12 to expose the pusher bar 22, indicating that the medical injector apparatus 100 has been used, and should be discarded after use.

FIG. 2 shows the medical injector apparatus 100 of FIG. 1 in a side elevational view. This view also shows the medical injector 100 having the safety guard 10 secured to the housing 18 with opposing hinge portion 12.

FIG. 3 is a sectional view of the medical injector apparatus 100, taken along line 3—3 of FIG. 2. In this view, the wedge shaped member 60, spring means 25 and pusher bar 22 are entirely visible. As seen in FIG. 3, the safety guard 10 located atop the housing 18 protects a pusher bar 22 from accidentally being depressed. The pusher bar 22 is not attached to the housing 18, however, and is free to slidably move between the first casing side 20 and the second casing side 30, against the biasing force of the spring means 25. The spring means 25 may be any known spring means 25, such as a leaf spring, resilient sponge material, coil spring, resilient tab, etc., and all such spring means are intended to be included within the scope of this invention, and the following claims.

The pusher bar 22 is connected to a column 24 which passes through an aperture (such as a bore) in the stationary bar 23. The stationary bar 23 is thus not moved by actuation of the pusher bar 22. The column 24 is connected at one end to the pusher bar 22, and at the opposite end directly to the wedge-shaped member 60. The pusher bar 22, column 24, and the wedge-shaped member 60 therefore move together as a unit when the pusher bar 22 is pushed in a dispensing direction.

A spring means 25 is preferably disposed between the stationary bar 23 and the pusher bar 22, to resiliently bias the pusher bar 22 away from the fluid 42, so as to be in a non-dispensing condition. The wedge-shaped member 60 has inclined sides 61 shaped to conform to the inclined sides 31 of the lower casing 30. The wedge-shaped member 60 may be inclined to allow a small amount of medication to remain in the wedge shaped reservoir 62 when the wedge shaped member 60 is fully depressed, ensuring that air is not injected when the wedge shaped member 60 is fully depressed. The wedge-shaped reservoir 62 is formed within the chamber 28 formed between the first casing side 20, the second casing side 30, the inclined sides 61 of the wedge shaped member 60, and the inclined sides 31 of the lower casing portion 30. The medication fluid 42 is disposed within the wedge shaped reservoir 62 formed between the wedge-shaped member 60 and the housing 18. This space is thus a precisely defined volume, containing a precise amount of the medication fluid 42.

The bottom portion 34 of the housing 18 also includes a bore 35 extending between the chamber 28 and the bottom portion of the housing 34. The bore 35 is sized to closely receive a resilient sleeve 33 therein. The resilient sleeve 33 is preferably made of rubber or plastic. The resilient sleeve 33 includes a top flange 36, side walls 37 sized to slidably receive the needle 70, and a bottom portion for sealing the needle 70 therein. The needle 70 is secured into the wedge-shaped member 60. The needle 70 passes through the bottom portion 34 of the resilient sleeve 33 when the pusher bar 22 is depressed. This advances the needle beyond the bottom portion 34 of the housing 18, exposing the needle tip 74 for injection of the medication fluid 42, into a user. When the pusher bar 22 is released, the biasing means 25, such as a spring, raises the pusher bar 22, which in turn raises the wedge shaped member 60, which also raises the needle into the protective custody of the resilient sleeve 33.

The needle 70 includes a needle aperture 72 to pass medication fluid 42 into the needle 70 as the wedge shaped member 60 is depressed. The needle aperture 72 is exposed to the medication fluid 42 within the wedge shaped reservoir 62, to permit flow of the fluid 42 through the needle aperture 72, and out through the needle tip 74 when the pusher bar 22 is depressed. For example, the needle 70 can have a slit aperture 72 extending longitudinally, so that even though the needle 70 slit aperture 72 passes partially into the resilient sleeve 33, the needle 70 can continue to receive the fluid 42, as the wedge shaped member 60 is depressed towards the bottom portion 34 of the housing 18. Depression of the pusher bar 22 extends the needle tip 74 beyond the bottom portion 34 of the housing 18 where the needle tip 74 is subsequently injected into the user.

The needle 70, in its retracted position shown in FIG. 3, is preferably slightly shorter than the length of the resilient sleeve 33, so that the needle tip 74 which would be otherwise exposed to the ambient air is instead preferably sealed within the resilient sleeve 33, which may be very snug and self-sealing in the absence of applied pressure on the pusher bar 22.

FIG. 4 is a sectional view taken along line 4—4 of FIG. 3, showing the needle tip 74 contained within the resilient sleeve 33. In FIG. 6, the needle tip 74 has been actuated so that it projects from the bottom portion 34 of the housing 18. The wedge-shaped member 60 is depressed until the inclined sides 61 abut the inclined sides 31 of the lower casing 30, dispensing a fixed quantity of medication fluid 42 from the wedge shaped reservoir 62 through the needle tip 74 into the user. As previously noted, the inclined sides 61 of the wedge shaped member 60 may be slightly modified to allow some medication to remain in the wedge shaped reservoir 62 when the pusher bar 23 is filly depressed. This ensures that air will not be inadvertently injected with the medication.

To use, the bottom portion 34 of the medical injector apparatus 100 is placed against the user at the desired injection location, breakable seal 41 is removed, and the safety guard 10 is pivoted to expose the pusher bar 22, and the pusher bar 22 is depressed to lower the needle tip 74 beyond the bottom portion 34 of the housing 18. The medication fluid 42 from within the wedge shaped reservoir 62 is forced through the aperture 72 in the needle 70 by the wedge shaped member 60, as the pusher bar 22 is depressed. This may be done directly against the user's skin, or directly through the user's clothing. This avoids the embarrassment of exposing the user's skin at the time of the injection, which is helpful when others are present at the time of the injection. There is a positive tactile feel, when the inclined sides 61 of the wedge shaped member 60 abut the inclined sides 31 of the lower casing 30.

Once the injection has been completed, the pusher bar is released, allowing the spring means 25 to safely reposition the needle tip 74 within the resilient sleeve 33. The safety guard 10 is then pivoted over the pusher bar 22 about hinge portions 12, 12 and secured into place, preventing accidental or inadvertent contact with the needle tip 74 during disposal of the medical injector apparatus 100. The medical injector apparatus 100 disclosed herein is intended to be used once, then discarded, for safety and to avoid possible contamination with a used needle 70.

The wedge-shaped member 60 is movable relative to the housing 18, despite the relatively tight fit, which is necessarily tight in order to form a fluid-tight seal between the wedge-shaped member 60 and the interior walls 29 of the housing 18. A resilient seal 76 may be used between the stationary bar 23 and the wedge shaped member 60 to aid in sealing the medication fluid 42 within the wedge shaped reservoir 62.

FIG. 5 is an enlarged sectional view of the pusher bar 22, column 24, the stationary bar 23, and at least one spring means 25, taken along line 5—5 of FIG. 3. As seen, column 24 passes through a column aperture 21 in the stationary bar 23. The spring means 25 is preferably disposed on both sides of the column 24, so that, when pressure on the pusher bar 22 is released, the pusher bar 22 is raised, thereby retracting the needle 70 into the housing 18. Thus, the medical injector apparatus 100, once used, presents no accidental sharps hazard during disposal of the medical injector apparatus 100.

FIG. 6 is a side elevational view of the bottom portion 34 of the housing 18 of the medical injector apparatus 100 of FIG. 1. In FIG. 6, the needle tip 74 is shown in its fully extended position, with the needle tip 74 projecting from the bottom portion 34 of the housing 18. As soon as pressure on the pusher bar 22 is released, the needle tip 74 is retracted into the housing 18, ensuring safe disposal of the medical injector apparatus 100 after use.

As seen in FIG. 1, the first casing 20 preferably has a window 40 therein, at a location in alignment with the medication fluid 42 when the pusher bar 22 is not depressed. Thus, the window 40 permits the medication fluid 42 to be viewed through the window 40, enabling the user to determine if the medication fluid 42 has been previously dispensed. The window 40 also permits the user to see if the medication fluid 42 has changed color, or evaporated. Preferably, the window 40 is treated to provide UV resistance, when light sensitive or UV sensitive medication fluid 42 is placed within the medical injector apparatus 100.

A seal means 41 may be secured between the safety guard 10 and the housing 18. The seal means 41 is used to secure the safety guard 10 in place over the pusher bar 22, in its raised position. The seal means 41 is broken, biased or removed to enable the safety guard 10 to pivot about hinge portions 12,12 to expose the pusher bar 22. When the seal means 41 is broken, biased or removed, it is apparent that the medical injector apparatus 100 has been used, and should not be reused. When the safety guard 10 is returned to its protective position over the pusher bar 22, there is no danger of accidentally or inadvertently depressing the pusher bar 22. This ensures that the needle 70 will remain above the lower casing 30. The seal means 41 may be any known type seal, such as an adhesive strip used to secure medication within a container, prior to use.

The safety guard 10 can be adapted to snap lock in place in a manner well known in the art to further protect the pusher bar 22 from being accidentally depressed after use.

The length and width of the housing 18 is preferably sized to be similar to the length and width of a credit card (not shown), and the thickness of the housing 18 is sized to be less than one inch, for ease of transport and storage.

The housing 18 may be adapted to comprise a central housing member 80, with the central housing member 80 shaped to provide a wedge shaped reservoir 62 located beneath a stationary bar 23, as shown in FIG. 7. In this adaptation, the first casing side 20 is secured to a one side of the central housing member 80, and the second casing side 30 secured to the opposite side of the central housing member 80. The first and second casing sides 20, 30 enclosing the wedge shaped reservoir 62 therebetween.

Indicia 78 is positioned on at least one of the first casing side 20 and the second casing side 30. The indicia 78 preferably includes information relating to the type of medication fluid 42 stored within the medical injector apparatus 100, and instructions relating to the use and disposal of the medical injector apparatus 100.

The invention being thus described in the form of a preferred embodiment, it will be evident that the invention may be varied in many ways. Such variations are not to be regarded as a departure from the spirit and scope of the invention and all such modifications are intended to be included within the scope of the claims.

PARTS LIST

100—medical injector apparatus
10—safety guard
12—hinge portions
18—housing
20—first casing side
21—column aperture
22—pusher bar
23—stationary bar
24—column
25—spring means
26—flexible seal
28—fluid chamber 28
29—interior walls
30—second casing side
31—inclined sides
32—top portion
33—resilient sleeve
34—bottom portion
35—bore
36—top flange
37—side walls
38—bottom portion
40—window
41—seal means
42—medication fluid
60—wedge shaped member
61—inclined sides of wedge shaped member
62—wedge shaped reservoir
70—needle
72—needle aperture 74—needle tip
76—resilient seal
78—indicia
80—central housing member

What is claimed is:

1. A compact medical injector apparatus, which comprises:
   a) a first casing portion having a front side, left side, right side, bottom side and top side, the first casing portion further having a stationary bar with a column aperture extending therethrough;
   b) a second casing portion having a back side, left side, right side, bottom side and top side, the second casing portion further having a stationary bar with a column aperture extending therethrough; the second casing portion secured to the first casing portion to form a housing with a fluid chamber therebetween;
   c) a pusher bar slidably received on the top side of the housing between the first casing portion and the second casing portion at a location above the stationary bar;
   d) a wedge shaped member connected to the pusher bar by a column, the wedge shaped member slidably received in a wedge shaped reservoir within the fluid chamber located between the first and second casing portions at a location below the stationary bar, the fluid chamber further having a bore extending between the fluid chamber and the bottom portion of the housing;
   e) a liquid dispensing needle secured to the wedge shaped member, with a fluid receiving port positioned on the dispensing needle, the fluid receiving port extending within the dispensing chamber;
   f) a biasing means to raise the pusher bar, the wedge shaped member, and the dispensing needle into a raised, non-dispensing position;
   g) a resilient sleeve positioned within the bore provided, the resilient sleeve having a top flange, with side walls sized to slidably receive the dispensing needle therethrough, the resilient sleeve further with a bottom portion to seal the dispensing needle within the wedge shaped reservoir, until the dispensing needle is pushed through the bottom portion when the pusher bar is manually depressed against the biasing means, to extend the needle beyond the bottom portion of the housing; and
   h) a safety guard is pivotally positioned on the top portion of the housing to cover the pusher bar in a non-use position, and the safety guard is pivotally positioned to access the pusher bar in an at-use position, the safety guard to protect against inadvertent actuation of the pusher bar.

2. The compact medical injector apparatus of claim 1, wherein a viewing window is provided in the housing adjacent to the wedge shaped reservoir, to provide a visual indication of the presence of medication fluid within the medical injector apparatus.

3. The compact medical injector apparatus of claim 2, wherein the seal means is a breakable seal which extends between the housing and the safety guard, and said breakable seal means provides a visual indication when the seal means is broken, and the medical injector apparatus has been used.

4. The compact medical injector apparatus of claim 1, wherein the length and width of the housing is sized to be similar to the length and width of a credit card, and the thickness of the housing is sized to be less than one inch thick, for ease of transport and storage between use.

5. The compact medical injector apparatus of claim 1, wherein a resilient seal is provided between the wedge shaped member and the stationary bar on the housing to seal the liquid medication within the wedge shaped reservoir.

6. The compact medical injector apparatus of claim 1, wherein the housing comprises a central housing member, with the central housing member shaped to provide a wedge shaped reservoir located beneath a stationary bar, the first casing side secured to a one side of the central housing member, and the second casing side secured to the opposite side of the central housing member, the first and second casing sides positioned to enclose the wedge shaped reservoir therebetween.

7. The compact medical injector apparatus of claim 1, wherein indicia is positioned on at least one of the first casing side and the second casing side, and said indicia includes information relating to the fluid medication stored within the medical injector apparatus, and instructions relating to the use and disposal of the medical injector apparatus.

8. The compact medical injector apparatus of claim 1, wherein the spring means comprises one of: a leaf spring, a coiled spring, a resilient spacer and a resilient foam member.

9. The compact medical injector apparatus of claim 1, wherein the safety guard comprises a U-shaped member having a top portion and depending side portions, with apertures extending in axial alignment through the depending side portions, and pins extending through the apertures to rotatably secure the safety guard to the housing.

10. A compact medical injector apparatus, which comprises:
    a) a first casing portion having a front side, left side, right side, bottom side and top side, the first casing portion further having a stationary bar with a column aperture extending therethrough;
    b) a second casing portion having a back side, left side, right side, bottom side and top side, the second casing portion further having a stationary bar with a column aperture extending therethrough; the second casing portion secured to the first casing portion to form a housing with a fluid chamber therebetween;
    c) a pusher bar slidably received on the top side of the housing between the first casing portion and the second casing portion at a location above the stationary bar;
    d) a wedge shaped member connected to the pusher bar by a column, the wedge shaped member slidably received in a wedge shaped reservoir within the fluid chamber located between the first and second casing portions at a location below the stationary bar, the fluid chamber further having a bore extending between the fluid chamber and the bottom portion of the housing;
    e) a liquid dispensing needle secured to the wedge shaped member, with a fluid receiving port positioned on the dispensing needle, the fluid receiving port extending within the dispensing chamber;
    f) a biasing means to raise the pusher bar, the wedge shaped member, and the dispensing needle into a raised, non-dispensing position;
    g) a resilient sleeve positioned within the bore provided, the resilient sleeve having a top flange, with side walls sized to slidably receive the dispensing needle therethrough, the resilient sleeve further with a bottom portion to seal the dispensing needle within the wedge shaped reservoir, until the dispensing needle is pushed through the bottom portion when the pusher bar is manually depressed against the biasing means, to extend the needle beyond the bottom portion of the housing;
    h) a safety guard is pivotally positioned on the top portion of the housing to cover the pusher bar in a non-use position, and the safety guard is pivotally positioned to access the pusher bar in an at-use position, the safety guard to protect against inadvertent actuation of the pusher bar; and i) a viewing window is provided in the housing adjacent to the wedge shaped reservoir, to provide a visual indication of the presence of medication fluid within the medical injector apparatus.

11. The compact medical injector apparatus of claim 10, wherein the seal means is a breakable seal which extends between the housing and the safety guard, and said breakable seal means provides a visual indication when the seal means is broken, indicating that the medical injector apparatus has been used.

12. The compact medical injector apparatus of claim 10, wherein the length and width of the housing is sized to be similar to the length and width of a credit card, and the thickness of the housing is sized to be less than one inch thick, for ease of transport and storage between use.

13. The compact medical injector apparatus of claim 10, wherein a resilient seal is provided between the wedge shaped member and the stationary bar on the housing to seal the liquid medication within the wedge shaped reservoir.

14. The compact medical injector apparatus of claim 10, wherein the housing comprises a central housing member, with the central housing member shaped to provide a wedge shaped reservoir located beneath a stationary bar, the first casing side secured to a one side of the central housing member, and the second casing side secured to the opposite side of the central housing member, the first and second casing sides enclosing the wedge shaped reservoir therebetween.

15. The compact medical injector apparatus of claim 10, wherein indicia is positioned on at least one of the first casing side and the second casing side, and said indicia includes information relating to the fluid medication stored within the medical injector apparatus, and instructions relating to the use and disposal of the medical injector apparatus.

16. The compact medical injector apparatus of claim 10, wherein the spring means comprises one of: a leaf spring, a coiled spring, a resilient spacer and a resilient foam member.

17. The compact medical injector apparatus of claim 10, wherein the safety guard comprises a U-shaped member having a top portion and depending side portions, with apertures extending in axial alignment through the depending side portions, and pins extending through the apertures to rotatably secure the safety guard to the housing.

18. A compact medical injector apparatus, which comprises:

a) a first casing portion having a front side, left side, right side, bottom side and top side, the first casing portion further having a stationary bar with a column aperture extending therethrough;

b) a second casing portion having a back side, left side, right side, bottom side and top side, the second casing portion further having a stationary bar with a column aperture extending therethrough; the second casing portion secured to the first casing portion to form a housing with a fluid chamber therebetween;

c) a pusher bar slidably received on the top side of the housing between the first casing portion and the second casing portion at a location above the stationary bar;

d) a wedge shaped member connected to the pusher bar by a column, the wedge shaped member slidably received in a wedge shaped reservoir within the fluid chamber located between the first and second casing portions at a location below the stationary bar, the fluid chamber further having a bore extending between the fluid chamber and the bottom portion of the housing;

e) a resilient seal is provided between the wedge shaped member and the stationary bar on the housing to seal the liquid medication within the wedge shaped reservoir;

f) a liquid dispensing needle secured to the wedge shaped member, with a fluid receiving port positioned on the dispensing needle, the fluid receiving port extending within the dispensing chamber;

g) a biasing means to raise the pusher bar, the wedge shaped member, and the dispensing needle into a raised, non-dispensing position;

h) a resilient sleeve positioned within the bore provided, the resilient sleeve having a top flange, with side walls sized to slidably receive the dispensing needle therethrough, the resilient sleeve further with a bottom portion to seal the dispensing needle within the wedge shaped reservoir, until the dispensing needle is pushed through the bottom portion when the pusher bar is manually depressed against the biasing means, to extend the needle beyond the bottom portion of the housing;

i) a safety guard is pivotally positioned on the top portion of the housing to cover the pusher bar in a non-use position, and the safety guard is pivotally positioned to access the pusher bar in an at-use position, the safety guard to protect against inadvertent actuation of the pusher bar; and p) a viewing window is provided in the housing adjacent to the wedge shaped reservoir, to provide a visual indication of the presence of medication fluid within the medical injector apparatus.

19. The compact medical injector apparatus of claim 18, wherein the seal means is a breakable seal which extends between the housing and the safety guard, and said breakable seal means provides a visual indication when the seal means is broken, and the medical injector apparatus has been used.

20. The compact medical injector apparatus of claim 18, wherein the length and width of the housing is sized to be similar to the length and width of a credit card, and the thickness of the housing is sized to be less than one inch thick, for ease of transport and storage between use.

21. The compact medical injector apparatus of claim 18, wherein the housing comprises a central housing member, with the central housing member shaped to provide a wedge shaped reservoir located beneath a stationary bar, the first casing side secured to a one side of the central housing member, and the second casing side secured to the opposite side of the central housing member, the first and second casing sides enclosing the wedge shaped reservoir therebetween.

22. The compact medical injector apparatus of claim 18, wherein indicia is positioned on at least one of the first casing side and the second casing side, and said indicia includes information relating to the fluid medication stored within the medical injector apparatus, and instructions relating to the use and disposal of the medical injector apparatus.

23. The compact medical injector apparatus of claim 1, wherein the spring means comprises one of: a leaf spring, a coiled spring, a resilient spacer and a resilient foam member.

24. The compact medical injector apparatus of claim 1, wherein the safety guard comprises a U-shaped member having a top portion and depending side portions, with apertures extending in axial alignment through the depending side portions, and pins extending through the apertures to rotatably secure the safety guard to the housing.

* * * * *